United States Patent [19]
Borland et al.

[11] Patent Number: 5,292,954
[45] Date of Patent: Mar. 8, 1994

[54] AMINE OXIDE COMPOSITION AND PROCESS

[75] Inventors: James E. Borland; Joe D. Sauer; Kim R. Smith, all of Baton Rouge, La.

[73] Assignee: Ethyl Corporation, Richmond, Va.

[21] Appl. No.: 627,982

[22] Filed: Dec. 17, 1990

Related U.S. Application Data

[62] Division of Ser. No. 524,497, May 17, 1990, abandoned.

[51] Int. Cl.$^5$ ............................................. C07C 291/02
[52] U.S. Cl. ..................................... 564/298; 564/297; 564/463
[58] Field of Search ................ 564/298, 297; 252/547; 260/404

[56] References Cited

U.S. PATENT DOCUMENTS 3,565,810  2/1971  Mausher et al. ................... 564/297
4,748,275  5/1988  Smith et al. ........................ 564/298

FOREIGN PATENT DOCUMENTS 56061349  5/1981  Japan .
1087413  10/1967  United Kingdom .

*Primary Examiner*—Glennon H. Hollrah
*Assistant Examiner*—Shailendra Kumar
*Attorney, Agent, or Firm*—Patricia J. Hogan

[57] ABSTRACT

A pourable amine oxide composition which is suitable for use in detergent compositions is obtained by reacting a tert-amine with aqueous hydrogen peroxide in a nonionic surfactant as the sole organic solvent, at least a portion of the nonionic surfactant being an alkylphenol ethoxylate or other compound corresponding to the formula $Z[OC(Z')HCH_2]_mOH$ in which Z is an alkylphenyl group wherein the alkyl group contains 4-30 carbons, Z' is hydrogen or an alkyl or hydroxyalkyl group containing 1-3 carbons, and m is an integer of 1-100. When the composition has a low water content, it is suitable for use in water-sensitive formulations, such as bar soaps and detergent concentrates.

12 Claims, No Drawings

AMINE OXIDE COMPOSITION AND PROCESS

This application is a division of application Ser. No. 524,497, filed May 17, 1990, now abandoned.

FIELD OF INVENTION

This invention relates to amine oxide compositions and more particularly to such compositions suitable for incorporation into water-sensitive detergent formulations and to processes for preparing them.

BACKGROUND

As disclosed in Kirk-Othmer, Encyclopedia of Chemical Third Edition, Volume 2, pp. 259-271, it is known that amine oxides which are useful in various applications, such as detergent and shampoo formulations, can be prepared by reacting non-heterocyclic tert-amines with aqueous hydrogen peroxide in a solvent such as water, a lower alcohol, acetone, or acetic acid.

Copending application Ser. No. 415,910 (Smith et al.), filed Oct. 2, 1989, teaches that it is also possible to prepare the amine oxides as solid, non-hygroscopic dihydrates by conducting their syntheses in organic solvents, such as esters, hydrocarbons, and highly polar solvents, in which the products are soluble at reaction temperatures but insoluble at a lower temperature.

These amine oxides, which are generally trialkylamine oxides, particularly trialkylamine oxides containing both short and long alkyl groups, are sometimes utilizable as prepared. However, the solid amine oxides present handling problems; and the solvents used in the known syntheses of amine oxides, especially the flammable solvents and water, are apt to be undesirable in some applications. Moreover, even when not undesirable because of making a harmful contribution, such as an excess of water in a water-sensitive formulation, the solvents have the unattractive feature of contributing weight and bulk to amine oxide-containing formulations without serving a useful purpose therein.

It would be advantageous to be able to provide amine oxide compositions which could be poured or pumped from the vessels in which they are prepared to combine them with other ingredients of formulations in which they are to be incorporated, e.g., water-sensitive formulations, without having them in conjunction with solvents that would serve no useful function in the formulations and could be deleterious.

U.S. Pat. No. 3,565,810 (Mausner et al.) shows a recognition of some of these problems and an attempt to solve them, but its process uses so much water that its products have too much unnecessary bulk and weight and would not be suitable for incorporation into water-sensitive formulations.

SUMMARY OF INVENTION

It has now been found that compositions having a high surfactant content can be obtained by conducting at least the latter part of the reaction of a tert-amine with aqueous hydrogen peroxide to form an amine oxide in the presence of a nonionic surfactant as the sole organic solvent; at least a portion of the nonionic surfactant being a compound corresponding to the formula $Z[OC(Z')HCH_2]_mOH$ in which Z is an alkylphenyl group in which the alkyl group contains 4-30 carbons, Z' is hydrogen or an alkyl or hydroxyalkyl group containing 1-3 carbons, and m is an integer of 1-100.

It has also been found that the use in the process of a fairly highly concentrated hydrogen peroxide solution and/or the removal of at least a portion of the water from the final reaction mixture can provide a pourable liquid blend of a tert-amine oxide and a solvent consisting essentially of a nonionic surfactant solvent and 0-30% by weight of water, a blend which is suitable for easy incorporation into water-sensitive formulations such as bar soaps and detergent compositions.

DETAILED DESCRIPTION

The amine used in the practice of the invention may be any tert-amine that can be oxidized to a tert-amine oxide with aqueous hydrogen peroxide. Such amines are well known and include a variety of tert-amines having aliphatic, cycloaliphatic and/or aromatic groups attached to the amino nitrogen. However, they are generally trialkylamines corresponding to the formula RR'R"N wherein R, R', and R" are primary alkyl groups containing 1-30 carbons, preferably such trialkylamines in which R is methyl or ethyl, R' is an alkyl group containing 6-20 carbons, and R" is independently selected from methyl, ethyl, and alkyl groups containing 6-20 carbons.

Exemplary of the tert-amines that may be used are trimethylamine, triethylamine, N-isobutyldimethylamine, trihexylamine, N,N-dimethyl-2-ethylhexylamine, N-eicosyldimethylamine, N-isobutyl-N-triacontylmethylamine, N-benzyldimethylamine, N-ethyldibenzylamine, N,N-diisobutyl-4-t-butylbenzylamine, tri-2-hydroxyethylamine, N-dodecyldi-2-hydroxyethylamine, N,N-didecyl-2-hydroxyethylamine, and, more preferably, the N-alkyldimethyl-, N-alkyldiethyl-, N-alkyl-N-ethylmethyl-, N,N-dialkylmethyl-, and N,N-dialkylethylamines in which the alkyl groups are hexyl, octyl, decyl, dodecyl, tetradecyl, hexadecyl, octadecyl, and/or eicosyl, as well as mixtures of such amines.

The aqueous hydrogen peroxide which is reacted with the tert-amine may have a concentration of 1-99% by weight but, in a preferred embodiment of the invention, has a concentration of 50-70% by weight. The more dilute solutions are apt to contribute more water to the product than is desired in many instances, but the excess water may be removed from the product after completion of the reaction in those instances.

As in conventional tert-amine/hydrogen peroxide reactions, the amount of hydrogen peroxide employed should be at least the stoichiometric amount but generally not more than a 15% molar excess; and the reaction is conducted by adding the aqueous hydrogen peroxide to the amine, preferably at a controlled rate and preferably in the presence of carbon dioxide or a chelating agent, such as diethylenetriaminepentaacetic acid or ethylenediaminetetraacetic acid, at a temperature of about 20°-100° C., preferably 60°-80° C.; and the reaction temperature is maintained for 1-24 hours.

The process of the invention differs from the conventional processes in that at least the latter part of the reaction is conducted in the presence of a nonionic surfactant as the sole organic solvent. Although the presence of such a solvent in the initial reaction mixture would not prevent the reaction from occurring, it is generally preferred to initiate the reaction in the absence of the organic solvent and then to add it gradually during the reaction so as to maintain the reaction mixture stirrable and/or so as to provide an amine oxide/nonionic surfactant weight ratio of about 0.1-10/1 in the final reaction mixture.

The nonionic surfactant solvent employed in the process contains a compound corresponding to the formula $Z[OC(Z')HCH_2]_mOH$ in which Z is an alkylphenyl group wherein the alkyl group contains 4-30 carbons; Z' is hydrogen or an alkyl or hydroxyalkyl group containing 1-3 carbons, such as methyl, ethyl, propyl, hydroxymethyl, 2-hydroxyethyl, or 3-hydroxypropyl; and m is an integer of 1-100. This compound may comprise only a portion of the nonionic surfactant solvent. However, in a preferred embodiment of the invention, more than 50% by weight of the nonionic surfactant solvent, preferably at least substantially all of it, is composed of this compound.

Nonionic surfactants corresponding to the above formula are well-known compounds which can be prepared by reacting ethylene oxide or an alkyl- or hydroxyalkyl-substituted ethylene oxide with an alkylphenol in which the alkyl group contains 4-30 carbons or with a mixture of such alkylphenols. For use in the present invention, these compounds should be liquids; and the preferred compounds are those in which m is an integer not higher than about 50, preferably 2-15. Also preferred are the compounds prepared from ethylene oxide, i.e., those in which Z' is hydrogen. Particularly good results have been obtained by the use of a nonylphenol ethoxylate, e.g., such an ethoxylate in which the ethylene oxide unit/alkylphenol unit mol ratio is an average of nine; but good results are also obtained by the use of other compounds corresponding to the above formula, including those formed from one or more other alkylphenols in which the alkyl group contains 4-30 carbons, such as butyl-, isobutyl-, hexyl-, octyl-, nonyl-, decyl-, undecyl-, dodecyl-, tetradecyl-, hexa-, decyl-, octadecyl-, eicosyl-, docosyl-, tetracosyl-, and triacontylphenols.

When the surfactant corresponding to the above formula is not the only component of the nonionic surfactant solvent, the remainder may be composed of one or more liquid nonionic surfactants of any type. Exemplary of such other nonionic surfactants (which, like the aforementioned nonionic surfactants, are well known) are sorbitan oleates; sorbitan monolaurate; reaction products of sorbitan fatty acid esters with ethylene oxide; fatty acid (especially lauric) esters of glycols, such as ethylene glycol, diethylene glycol, and 1,2-propanediol; and compounds corresponding to the formulas $T[OC(Z')HCH_2]_mOH$, $TC(O)[OC(Z')HCH_2]_mOH$, and $TC(O)NZ'Z''$ wherein T is an alkyl group containing 4-30 carbons, Z'' is a hydroxyalkyl group containing 1-3 carbons, and Z' and m have the meanings given above.

Of these optional nonionic surfactants, those apt to be preferred are the alcohol ethoxylates, especially those prepared from one or more alcohols containing 6-12 carbons, e.g., a hexanol/decanol mixture; and the fatty acid amides containing one or two 2-hydroxyethyl groups and prepared from fatty acids such as lauric, linoleic, oleic, coco, stearic, and ricinoleic acids.

After completion of the reaction, the reaction mixture may be cooled to room temperature and, if necessary, then reheated to a fluidizing temperature when the reaction mixture is not fluid and it is desired to be able to pour or pump the reaction product from the vessel in which it was prepared. Alternatively, the reaction product may be poured or pumped from the reaction vessel before the temperature has been reduced to a point at which the product is no longer fluid when it is a product that is apt to gel at lower temperatures.

The amine oxide solution formed by the process contains water because of the use of the aqueous hydrogen peroxide. Since a small amount of water can be tolerated even in water-sensitive formulations in which it might be desired to incorporate the amine oxide, and the solutions containing relatively large amounts of water can be used in formulations which are not water-sensitive, it may not be necessary to remove any of the water in the solution. However, when the solution contains more water than is desired, it is removed from the reaction product by conventional means. The removal of the water may sometimes be accomplished by ordinary distillation, but the relatively low decomposition temperatures of some of the amine oxides makes it preferable to remove the water under reduced pressure to minimize the possibility of decomposing the product. Vacuum stripping is a particularly preferred method of removing at least a portion of the water from the product.

The invention is advantageous in that it provides amine oxide compositions having a high surfactant content that makes them attractive for incorporation into detergents, not only because of their surfactant content but because of their being pourable or pumpable. Moreover, the compositions having low water contents have those advantages as well as an ability to be used in water-sensitive formulations, such as bar soaps and detergent concentrates.

The following example is given to illustrate the invention and is not intended as a limitation thereof.

EXAMPLE

A suitable reaction vessel was charged with 100 g or N-tetradecyldimethylamine and 0.5 g of diethylenetriaminepentaacetic acid. After the mixture was heated to 65° C., 23 g of 70% hydrogen peroxide (a 15% molar excess) was added over a period or five minutes while cooling to prevent the temperature from rising further. The temperature was then raised to 75° C. and held there for approximately 24 hours while adding a 9-mol ethoxylate or nonylphenol as needed during the first seven hours to facilitate stirring. By the end of the seven hours, a total of 45 mL of the ethoxylate had been added, and the amine conversion was greater than 95%. The product was a gel which melted to a pumpable fluid near 40° C.

We claim:

1. In a process for preparing a tert-amine oxide by reacting a tert-amine with aqueous hydrogen peroxide, the improvement which comprises conducting at least the latter part of the reaction in the presence of a nonionic surfactant as the sole organic solvent; at least a portion of the nonionic surfactant being a compound corresponding to the formula $Z[OC(Z')HCH_2]_mOH$ in which Z is an alkylphenyl group wherein alkyl group contains 4-30 carbons, Z' is hydrogen or an alkyl or hydroxyalkyl group containing 1-3 carbons, and m is an integer of 1-100.

2. The process of claim 1 wherein the tert-amine is reacted at a temperature of 60°-80° C. with at least a stoichiometric amount of an aqueous hydrogen peroxide solution having a concentration of 50-70% by weight in the initial absence of the nonionic surfactant, which is added gradually during the reaction so as to maintain the reaction mixture stirrable.

3. The process of claim 2 wherein the amount of the nonionic surfactant added is such as to provide an amine oxide/nonionic surfactant weight ratio in the range of about 0.1–10/1 and a water content not higher than about 30% by weight in the final reaction mixture.

4. The process of claim 3 wherein the final water content is not higher than about 25% by weight.

5. The process of claim 4 wherein the final water content is not higher than about 10% by weight.

6. The process of claim 1 wherein at least a portion of the water in the mixture resulting from the reaction is removed under reduced pressure.

7. The process of claim 1 wherein the tert-amine is a compound corresponding to the formula RR'R"N in which R, R', and R" are primary alkyl groups containing 1–30 carbons.

8. The process of claim 7 wherein R is methyl or ethyl, R' is an alkyl group containing 6–20 carbons, and R" is independently selected from methyl, ethyl, and alkyl groups containing 6–20 carbons.

9. The process of claim 8 wherein R and R" are methyl.

10. The process of claim 1 wherein the compound corresponding to the formula $Z[OC(Z')HCH_2]_mOH$ is the sole nonionic surfactant solvent.

11. The process of claim 10 wherein Z' is hydrogen.

12. The process of claim 11 wherein m is an integer of 2–15.

* * * * *